United States Patent [19]

Buchner

[11] 4,135,139
[45] Jan. 16, 1979

[54] ULTRASONIC IMAGING APPARATUS OPERATING ACCORDING TO THE IMPULSE-ECHO METHOD

[75] Inventor: Klaus Buchner, Uttenreuth, Germany

[73] Assignee: Siemens Aktiengesellschaft, Berlin & Munich, Germany

[21] Appl. No.: 804,494

[22] Filed: Jun. 8, 1977

[30] Foreign Application Priority Data

Jun. 25, 1976 [DE] Fed. Rep. of Germany ....... 2628567

[51] Int. Cl.² .......................... G01S 9/66; G01S 7/62; A61B 10/00
[52] U.S. Cl. ..................................... 340/1 R; 73/626; 358/112; 128/2 V; 340/5 MP
[58] Field of Search .................... 340/1 R, 3 C, 5 MP; 73/625, 626, 628; 343/5 SC; 358/112, 140; 128/2 V

[56] References Cited
U.S. PATENT DOCUMENTS 3,790,925  2/1974  Ahrens ............................ 340/3 C X
4,010,466  3/1977  Hofstein ......................... 340/1 R X
4,024,490  5/1977  Wood et al. ..................... 340/3 C X Primary Examiner—Richard A. Farley
Attorney, Agent, or Firm—Hill, Gross, Simpson, Van Santen, Steadman, Chiara & Simpson

[57] ABSTRACT

In an illustrated embodiment the line generator for the image display device is operated at a relatively high frequency such as 200 Hz while the actual ultrasonic scanning takes place at a pulse repetition rate of 50 Hz. Preferably alternately operable buffer memories store successive lines of ultrasonic echo signals, and then provide readout of the lines at a higher rate consistent with the display line frequency. In the example given, each stored echo line is read out twice in successive display line intervals. By suitable control of the readout timing, one set of staggered pairs of display lines may be displayed during one image cycle, and an interleaved set of display line pairs may be activated during alternate image cycles in conjunction with interlaced scanning operation of the ultrasonic applicator.

10 Claims, 3 Drawing Figures

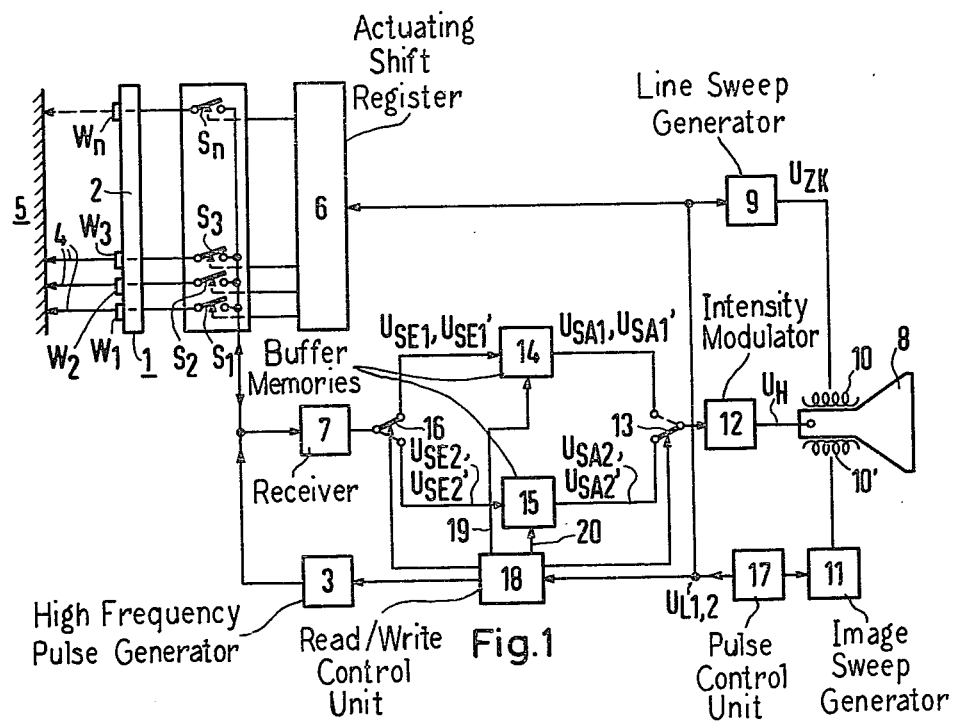
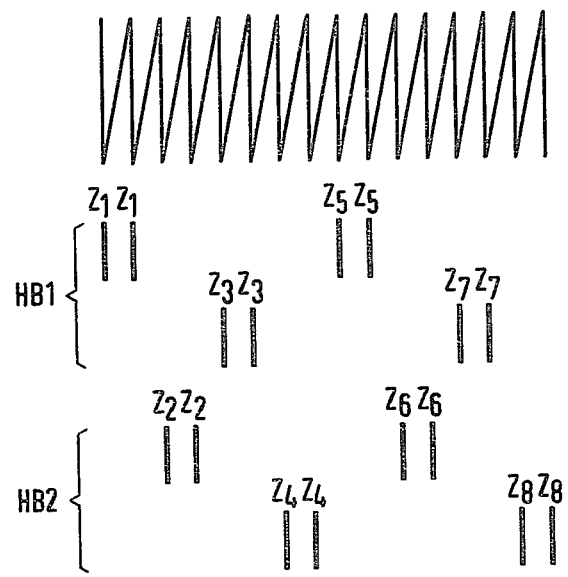
Fig.3

ULTRASONIC IMAGING APPARATUS OPERATING ACCORDING TO THE IMPULSE-ECHO METHOD

BACKGROUND OF THE INVENTION

The invention relates to an ultrasonic imaging apparatus operating according to the impulse-echo method, particularly intended for medical diagnostics, comprising an ultrasonic applicator for the linear ultrasonic scanning of an examination subject and an image display device with a line generator for the reproduction of the echo impulses as lines, as well as an image generator for the displacement of the line as a function of the displacement of the ultrasonic beam in the subject, whereby the ultrasonic scanning proceeds in partial images which are summated into the total image on the display device according to an interlaced scanning procedure.

An ultrasonic imaging apparatus of this type has already been proposed which operates with a total of three partial images which occur in succession and which are summated into the total image in an interlaced fashion according to an interlaced scanning procedure. The recording of each partial image on the display device (electron beam tube) proceeds with a deflection raster corresponding to that of the ultrasonic scanning in the examination subject for the respective partial image. There thus results on the image recording device a line sweep frequency for each partial image which amounts to only one-third of that particular sweep frequency which would have to be employed in the case of a total image recording procedure. Due to this strongly reduced line sweep frequency, particularly when the line density of each partial image is relatively low, the result can be the visual impression of a line raster running in a horizontal direction. Viewing of the image is consequently seriously disturbed.

SUMMARY OF THE INVENTION

It is the object of the present invention to disclose an ultrasonic imaging apparatus of the type initially cited which also operates according to the interlaced scanning method but wherein the above-cited disadvantage is eliminated.

In accordance with the invention, the object is achieved by virtue of the fact that the line and image generators of the image display device are so constructed and operated for the purpose of producing a line deflection raster during the occurrence of each partial image that the total number of lines occurring during each partial image display at least corresponds to the line number of the total image, intensity modulation by means of echo impulses proceeding, however, only in such lines of the deflection raster which are associated with the lines of that particular partial image, of the successively occurring partial images which is being displayed at that particular moment.

In the imaging apparatus according to the invention, the sweep frequency of the line deflection raster during each partial image cycle corresponds to that of the raster of a total image. Only the intensity modulation of the lines of the individual partial images proceeds according to the interlaced scanning procedure. Due to the high line deflection frequency of the line raster for each partial image, there results a line raster which is always stationary (motionless) even in the case of a relatively low line density per partial image.

Other objects, features and advantages of the present invention will be apparent from the following detailed description taken in connection with the accompanying sheets of drawings.

BRIEF DESCRIPTION OF THE DRAWINGS

FIG. 1 is a basic electric circuit diagram illustrating an ultrasonic imaging apparatus according to the invention;

FIG. 3 is a line diagram illustrating the line formation sequence on the display screen of the apparatus of FIG. 1.

DETAILED DESCRIPTION

Figure 2:
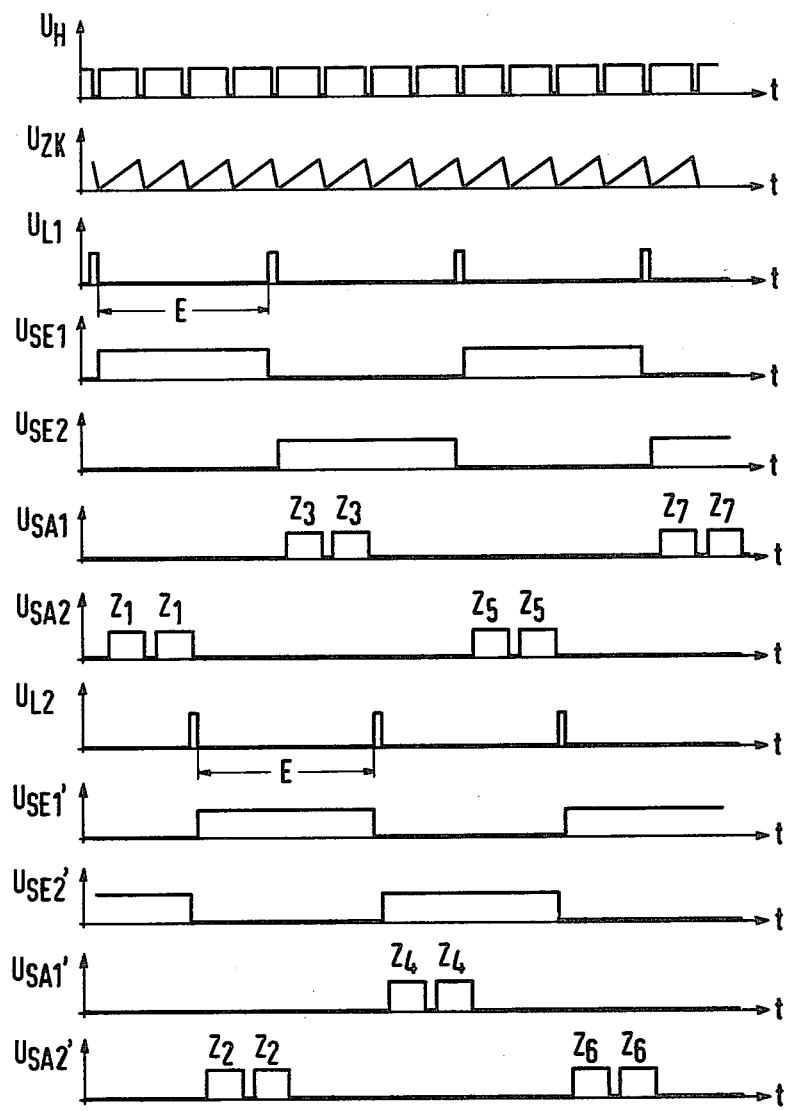
FIG. 2 is an impulse diagram illustrating the operation of the apparatus of FIG. 1 for carrying out a double interlaced scanning procedure.

In FIG. 1, reference numeral 1 designates an ultrasonic applicator which, in the present instance, is constructed in the form of an ultrasonic array. Accordingly, applicator 1 comprises a plurality of ultrasonic transducers $W_I$ through $W_n$ (piezoelectric crystal lamellae), which are supported adjacently of one another in a row on a carrier section 2 of a material having good ultrasonic wave-attenuating properties. The individual transducer elements $W_I$ through $W_n$ are capable of being selectively energized individually or in groups by high frequency impulses of a high frequency pulse generator 3 in such a manner that they radiate ultrasonic impulses in the direction of arrows 4 into an examination subject 5, e.g. a human body. The actuation of the individual transducer elements $W_I$ through $W_n$ in individual — or group-formation proceeds by means of an actuating mechanism comprising, in the conventional fashion, an actuating shift register 6 as well as actuating switches $S_I$ through $S_n$ for the purpose of connecting transducer elements which are to be energized to high frequency impulse generator 3 in the transmit mode, or connecting them to an echo impulse receiving amplifier 7 in the receive mode. The actuating mechanism operates with shift register 6 in such a manner that the individual transducer elements $W_I$ through $W_n$ can be switched to transmit or receive in continuous succession across the transducer row individually or in groups by means of correspondingly actuated switches $S_I$ through $S_n$. In this fashion, there is a resulting linear progression of the ultrasonic transmitting/receiving beam across the transducer row and a consequent corresponding linear ultrasonic scanning of the examination subject 5. In the sample embodiment according to FIG. 1, the ultrasonic scanning proceeds in the interlaced scanning procedure. Thus, it is for this reason that the transducer elements $W_I$ through $W_n$ of array 1 can be controlled by shift register 6 and actuating switches $S_I$ through $S_n$ such that, during a respective first scanning operation, the examination subject 5 is always scanned only in odd-numbered ultrasonic lines, respectively, and is scanned in the intermediate even-numbered ultrasonic lines only in the following second scanning operation. In this manner, two successive ultrasonic half-images result which must be correspondingly summated into a total image on an image recording device. In the present sample embodiment according to FIG. 1, specifically functioning as an image recording device there is an electron beam tube 8 with which is associated, in a conventional fashion a line sweep generator 9 for a horizontal deflection coil 10 as well as an image sweep generator 11 for the vertical deflection coil 10' of electron beam tube 8. Electron beam tube 8 further comprises an intensity modulator 12 for the purpose of intensity modulation ($U_H$) of the image lines in the rhythm of the echo impulses occurring. Intensity modulator 12 can be alternately connected to the readout outputs of a first buffer memory 14 and of a second buffer memory 15 by means of an alternate position changeover switch 13. An additional changeover switch 16, alternately positioned, in counter-rhythm correspondingly alternately connects the memory inputs (read-in inputs) of memories 14 or 15, respectively, with the echo impulse receiving amplifier 7. For the purpose of insuring a chronologically correct control of the transmit/receive cycles and line or image formation on the electron beam tube 8, there is a synchronous timing pulse control unit 17 which, by means of a proper chronological switch-over of changeover switches 13 or 16, respectively, is connected with a write/read control unit 18 for the write-in or read-out cycles of memories 14 or 15, respectively.

The mode of operation of the sample embodiment according to FIG. 1 will be apparent in conjunction with the impulse diagram according FIG. 2, as follows:

As previously stated above, scanning of the examination subject 5 with regard to the first half-image proceeds in odd-numbered scan lines, and, in the second cycle for the purpose of producing the second half-image, it proceeds correspondingly in even-numered scan lines. In order to form the first half-image, the timing pulse control unit 17 produces control pulses $U_{L1}$ according to FIG. 2, which control shift register 6 for the purpose of actuation of the respective switches $S_l$ through $S_n$ with the particular associated transducer elements $W_l$ through $W_n$ to the desired odd-numbered ultrasonic scan lines, on the one hand. On the other hand, each control pulse $U_{L1}$ also effects the release of an excitation pulse via the write/read-control unit 18 to the transmit pulse generator 3 for supply of a high frequency impulse to the actuated transducer element or elements $W_l$ through $W_n$. In addition, line sweep generator 9 is also triggered which executes a total of four line sweeps in the time interval between the occurrence of two successive control pulses. The ultrasonic-echo signals occurring in the transmit pauses between two transmit pulses — i.e., in the pauses between the control pulses $U_{L1}$ — coming from the examination subject 5 are delivered to the echo impulse-receiving amplifier 7 and from there they are alternately stored in the first buffer memory 14 or the second buffer memory 15 in the switch-over cadence of switch 16. The switching over of switch 16 proceeds in the cadence of switching pulses $U_{SE1}$ or $U_{SE2}$, pulse sequence $U_{SE1}$ determining the read-in time for occurring echo signals, into buffer memory 14, and pulse sequence $U_{SE2}$, correspondingly determining the read-in times of the echo impulses into buffer memory 15. The switching pulses for switch 16 are supplied by the write/read control unit 18. They are obtained in this control unit through a corresponding frequency division of the control clock pulse sequence $U_{L1}$ of timing-pulse control unit 17. In order to control the readout operation of the echo information stored in memories 14 or 15, respectively, there are corresponding switching pulses for switch 13 proceeding in counter rhythm relative to the write-in pulses $U_{SE1}$ or $U_{SE2}$, respectively. These switching pulses, in conjunction with call-up pulses supplied to the particular memory 14 or 15 which is switched to the readout operation via call-up lines 19 or 20, respectively, call-up stored line information $U_{SA1}$ or $U_{SA2}$, respectively. From the pulse diagram according to FIG. 2, it is clearly apparent that the readout times of echo information $U_{SA1}$ or $U_{SA2}$, respectively, from the particular memory 14 or 15, respectively, are substantially shorter than the duration of storing information into the memories, which is selected to be long corresponding to the substantially longer echo receiving time. Also clearly apparent is the counter-rhythm characteristic between echo impulse storage of echo impulses of a just previously scanned ultrasonic line into the one memory (e.g. memory 14) pursuant to a simultaneous call-up of the echo information from the preceding line which is stored in the other memory (e.g. memory 15) for the purpose of recording in the form of a corresponding image line on the display screen of the electron beam tube 8. In addition, it must be further noted that the call-up of echo signals proceeds according to a double call-up procedure; i.e., each line stored in a memory 14 or 15 is called up twice and correspondingly represented as a double line on the display screen of the electron beam tube 8. Such a method results in double the line number in the ultrasonic echo image. As mentioned, the formation of the first half image proceeds solely in odd-numbered scan lines. The construction of the second half image then proceeds in even-numbered scan lines. For this purpose, the timing pulse control unit 17 produces a further control clock pulse sequence $U_{L2}$ which, however, is now phase-delayed as compared with the control pulse sequence $U_{L1}$ of the first half image by half the echo receiving time E; i.e., by half the interval between two transmit control pulses. The storage-and read-out cycles of memories 14, or 15, respectively, then proceed in the cadence of this control clock pulse sequence $U_{L2}$, as in the case of the first half image, but with a corresponding phase delay. Thus there are consequent correspondingly phase-delayed storage cycles $U_{SE1}'$ or $U_{SE2}'$ for memories 14, or 15, respectively, with read-out cycles $U_{SA1}'$, and $U_{SA2}'$, correspondingly occurring in counter-rhythm. The readout of each stored line again proceeds twice. The characteristic of the line sweep voltage $U_{ZK}$ for the purpose of constructing the second half image corresponds to that of the first half image. Whereas, in the case of the first half image, recording of echo data on the display screen of the electron beam tube 8 proceeds by means of the respective first two line sweeps of line sweep voltage $U_{ZK}$ in the time interval of echo receiving time E, in the second half image there is a corresponding recording of the lines by means of the two last line sweeps in the echo receiving interval. In this manner, there thus results a total image of the ultrasonic scanning composed of the two half-images, wherein, in each particular instance, two double lines of the even-numbered scan lines come to be positioned directly between two double lines of the odd-numbered scan lines. The resulting image formation is once again illustrated in the line diagram according to FIG. 3 in the form of a time-composite representation of eight double lines with a total of sixteen sweep operations of the line sweep generator.

In the sample embodiment according to FIG. 1 through 3, the clock frequency of pulse control unit 17 and of the ultrasonic-transmit receive mode has been selected at preferably 50 Hz during each half image cycle. Accordingly, the line sweep of the line sweep generator 9 proceeds with the quadruple of this frequency; i.e., with 200 Hz. In utilizing the dual recording of lines, there thus may result an ultrasonic-echo image recording consisting of a total of 200 individual lines in the full image where the ultrasonic half-image corresponds to fifty ultrasonic impulses. Thus the number of raster lines (e.g. 200) which are produced by the control circuitry of FIG. 1 during the generation of each partial image by display unit 8 is at least equal to the total number of ultrasonic impulses per complete ultrasonic image frame (e.g. 100) and in the example given substantially exceeds this number.

In order to effect interlaced scanning of the ultrasonic applicator 1, it will be apparent to those skilled in the art that shift register 6 may have a first series of shift register stages associated with the odd numbered switches $S_1$, $S_3$, etc., and may have a second series of shift register stages associated with the even-numbered switches such as $S_2$. Then, during the first image cycle, the first shift register stage of the first series is set by means of a pulse corresponding to the first pulse $U_{L1}$ of FIG. 2, the successive pulses $U_{L1}$ from pulse control unit 17 serving to sequentially set the stages of the first series of shift register stages, so as to sequentially actuate the odd-numbered switches. Similarly, during the alternate image cycles, the first pulse $U_{L2}$ would serve to set the first stage of the second series of shift register stages so as to close switch $S_2$, and the successive pulses from pulse control unit 17 would then serve to sequentially activate the successive even-numbered switches. The pulse control unit 17 may include a pulse divider for supplying pulses to image sweep generator 11 at the image repetition rate, and this output may also be utilized to gate the first pulse of the series $U_{L1}$ to the first stage of the first series of shift register stages, and to gate the first pulse of the series $U_{L2}$ to the first stage of the second series of shift register stages.

It will be apparent that many modifications and variations may be effected without departing from the scope of the novel concepts and teachings of the present invention.

I claim as my invention:

1. Ultrasonic imaging apparatus operating according to the impulse-echo method, intended particularly for medical diagnostics, comprising an ultrasonic applicator for the linear ultrasonic scanning of an examination subject and an image display device with a line generator for reproducing the echo impulses in the form of a line, as well as comprising an image generator for the displacement of the line as a function of the displacement of the ultrasonic beam in the subject, the ultrasonic scanning proceeding in the manner of partial images which are summated into the total image on the display device in an interlaced fashion according to an interlaced procedure, characterized in control circuitry for the line and image generators of the image display device being constructed for the purpose of producing a line deflection raster during each partial image cycle which at least corresponds in its total number of lines to the number of lines of the total image, the control circuitry controlling the display device to display echo impulses only in those lines of the deflection raster which are associated with the lines of a particular partial image of the successively occurring partial images during each partial image cycle.

2. Ultrasonic imaging apparatus according to claim 1, characterized in that the control circuitry comprises a buffer memory means providing readout of the echo impulses of each partial image, for the purpose of intensity modulation of the respective associated lines of the total image-line deflection raster, such readout proceeding in a linear fashion in an alernating buffer memory operation.

3. Ultrasonic imaging apparatus according to claim 2, characterized in that the buffer memory means comprises two buffer memories (14, 15) for the alternating buffer storage operation, into which the echo impulses of two successive lines of each partial image are alternately read-in, and from which they are again called up in a corresponding alternating fashion for the purpose of intensity modulation.

4. Ultrasonic imaging apparatus according to claim 3, characterized in that, in each particular instance during the period of reading-in of echo impulses of a line into one buffer memory, the echo impulses of the preceding line which are stored in the other buffer memory are read-out at least once for the purpose of intensity modulation.

5. Ultrasonic imaging apparatus according to claim 3, characterized in that, in each particular instance during the period of reading-in of echo impulses of a line into one buffer memory, the echo impulses of the preceding line which are stored in the other buffer memory are read-out at least twice in succession for the purpose of intensity modulation.

6. Ultrasonic imaging apparatus according to claim 2, characterized in that, with a readout time for the echo impulses of a line in the alternating buffer memory operation which readout time lies within the sweep time of a raster line sweep, the read-in time into the buffer memory means corresponds to a longer echo impulse receiving time.

7. Ultrasonic imaging apparatus according to claim 2, characterized in that, with a readout time for the echo impulses of a line in the alternating buffer memory operation which readout time lies within the sweep time of a raster line sweep, the read-in time into the buffer memory means amounts to an integral multiple of the sweep time of a raster line sweep.

8. Ultrasonic imaging device according to claim 6, characterized in that the control circuitry provides at least two line sweeps of the line deflection raster in the time intervals of the storage of echo impulses of a line into the buffer memory means, but that about four line sweeps of the line deflection raster occur in these time intervals for the purpose of multiple line recording.

9. Ultrasonic imaging apparatus according to claim 8, characterized in that the read-out cycles of the buffer memory means each corresponds to half the echo impulse receiving time, the memory write-in and read-out cycle of a half image, however, being phase-delayed by half the echo impulse receiving time, as compared with that of the other half image.

10. Ultrasonic imaging apparatus according to claim 9, characterized in that the phase displacement of both half images is effected by means of a corresponding mutual displacement of the transmit/receive cycles of the ultrasonic applicator by half the echo impulse receiving time.

* * * * *